US00PP22357P3

(12) United States Plant Patent
White

(10) Patent No.: US PP22,357 P3
(45) Date of Patent: Dec. 20, 2011

(54) APPLE TREE NAMED 'PREMA193'

(50) Latin Name: ***Malus domestica* Mill.**
Varietal Denomination: PremA193

(75) Inventor: Allan G. White, Havelock North (NZ)

(73) Assignee: Prevar Limited, Hastings (NZ)

( * ) Notice: Subject to any disclaimer, the term of this patent is extended or adjusted under 35 U.S.C. 154(b) by 0 days.

(21) Appl. No.: 12/660,406

(22) Filed: Feb. 24, 2010

(65) Prior Publication Data

US 2010/0229266 P1 Sep. 9, 2010

Related U.S. Application Data

(60) Provisional application No. 61/208,863, filed on Feb. 26, 2009.

(51) Int. Cl.
*A01H 5/00* (2006.01)

(52) U.S. Cl. ..... Plt./161

(58) Field of Classification Search ..... Plt./161
See application file for complete search history.

*Primary Examiner* — June Hwu
(74) *Attorney, Agent, or Firm* — Ballew Law

(57) ABSTRACT

'PremA193' is a new and distinct apple tree (*Malus domestica* Mill.) notable for its attractive blush color and excellent flavor and texture.

2 Drawing Sheets

Genus and species: *Malus domestica* Mill.
Variety denomination: 'PremA193'.

CROSS-REFERENCE TO RELATED APPLICATIONS

Provisional application No. 61/208,863, filed on Feb. 26, 2009.

STATEMENT REGARDING FEDERALLY SPONSORED RESEARCH OR DEVELOPMENT

None

BACKGROUND AND SUMMARY OF THE VARIETY

The new variety of apple tree 'PremA193' was created in the course of a planned breeding program carried out in Hawkes Bay, New Zealand. 'PremA193' originated as a result of a controlled cross of 'Braeburn' (not patented, seed parent) and 'Tenroy' (U.S. Plant Pat. No. 4,121, pollen parent). 'PremA193' was selected as a single plant from among a population of seedlings derived from the parents, and was selected for its attractive fruit and its excellent flavor and texture. It is distinguished from its parents and the related cultivar 'Scifresh' (U.S. Plant Pat. No. 13,888) in its time of flowering. In Hawkes Bay, New Zealand Braeburn flowers early whereas 'Tenroy' flowers late and 'PremA193' flowers in mid season at the same time as 'Granny Smith'. The related cultivar 'Scifresh' flowers early. The harvest date (in Hawkes Bay, New Zealand) for 'PremA193' is late March and for 'Royal Gala' (U.S. Plant Pat. No. 4,121) it is the third week of February. Fruit over color for 'PremA193' is a lighter and brighter color compared with 'Braeburn'. Asexual propagation by budding was first carried out in Havelock North, New Zealand. The variety has since been observed over a number of asexually propagated generations, and has been found to remain true to type.

BRIEF DESCRIPTION OF THE PHOTOGRAPHS

Figure 1:
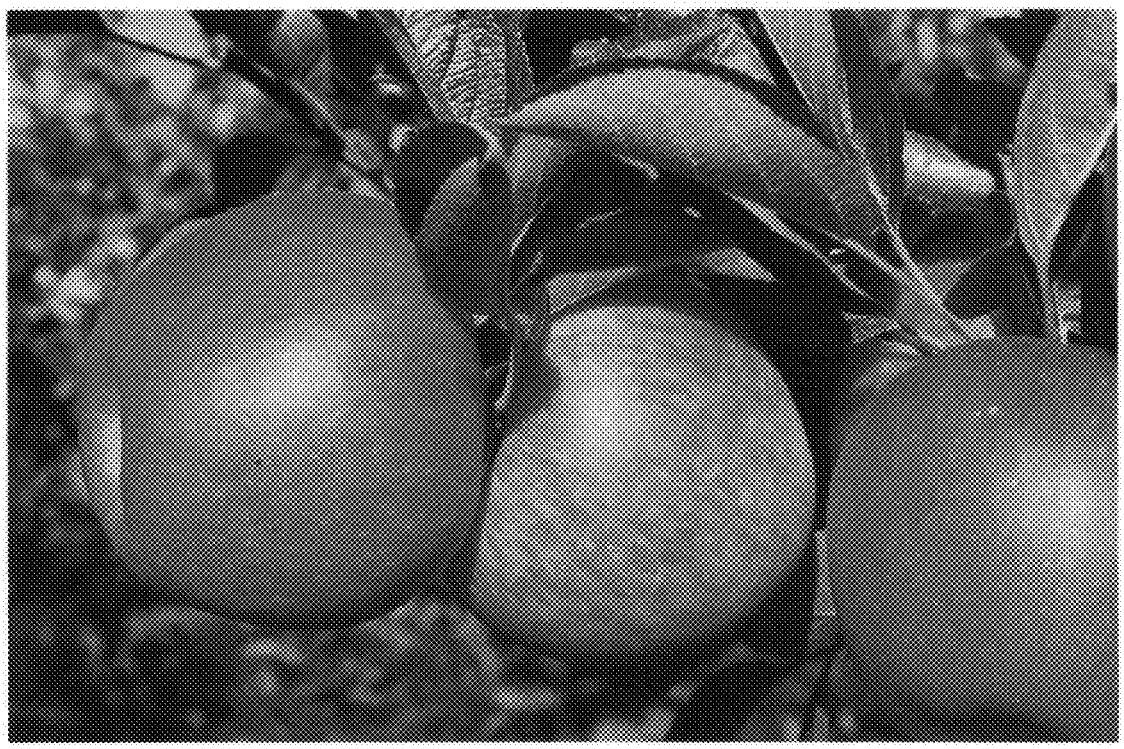
Figure 2:
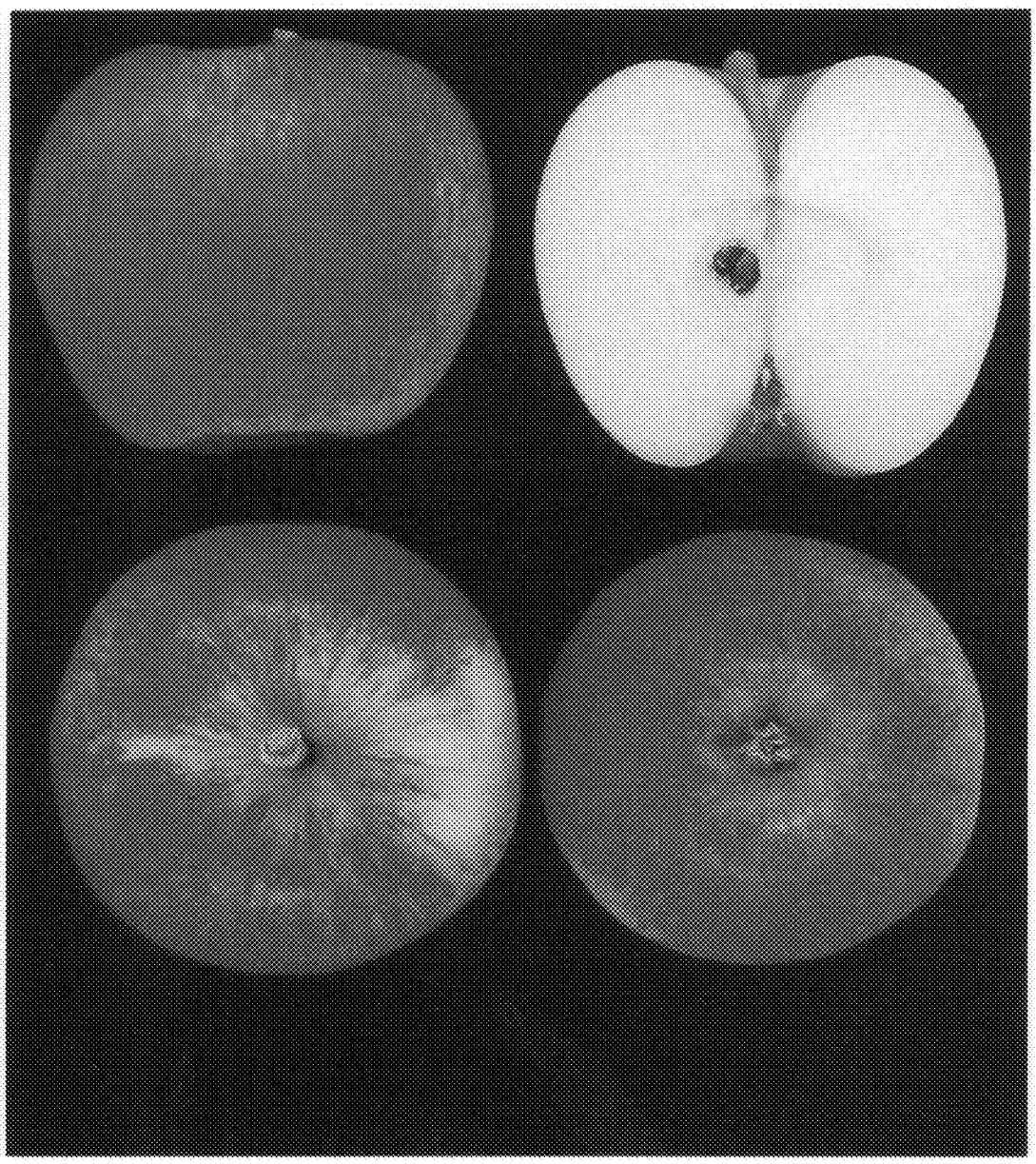

FIG. 1 shows the fruit and leaves of 'PremA193'; and
FIG. 2 shows whole and sectioned fruit of 'PremA193'.

DETAILED BOTANICAL DESCRIPTION

The following detailed botanical description is based on observations of ten year old 'PremA193' apple trees grown at Havelock North, New Zealand. Color descriptions refer to The Royal Horticultural Society Colour Chart, published in 2001. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:

*Vigor.*—Vigorous.
*Habit.*—Spreading.
*Bearing.*—Spurs and shoots.
*Size.*—Height: 2.4 m; spread 2.1 m.
*Trunk.*—Diameter: 13 cm at 30 cm above graft union; bark texture rough; color greyed-orange 166B.
*Trunk lenticels.*—Length 0.1 to 0.2 cm; color grey 201A.
*Branches.*—Length 1.0 m; diameter 0.8 to 2.2 cm; crotch angle 90°; color greyed-orange 166B (fruiting branch located about 1 m above graft union).
*Branch lenticels.*—Density 15 per square inch; length 0.1 to 0.2 cm; color grey 201A.
*Winter hardiness.*—Hardy in Hawkes Bay, New Zealand.

Dormant one year old shoot:

*Size.*—Diameter 1.0 to 1.5 cm; length 40 cm.
*Color.*—Greyed-orange 166C.
*Internode length.*—2.5 cm.

*Lenticels.*—Density 12 per square inch; length 0.1 cm; color grey 201B.

Flowers:

*Bud.*—Quantity per spur 5 to 6; length 1.4 cm; diameter 0.9 cm; color red-purple N57D with white 155C.

*Petals.*—Quantity per flower 5; Arrangement intermediate, touching; color white 155C and red purple N57D when fully open.

*Flower.*—Diameter 5.4 cm.

*Sepals.*—Quantity per flower 2; length 0.5 cm; color yellow-green 144B.

*Pedicel.*—Length 2.4 cm; diameter 0.2 cm; color yellow-green 144B.

*Anthers.*—Quantity per flower 11; length 0.1 cm; pollen color greyed-orange 163C.

*Stigma.*—Color greyed-orange 163C.

*Style.*—Length 0.9 cm; color yellow-green 145D.

*Ovary.*—Length 0.5 cm; color green 137D.

*Time of flowering.*—First week of October in Hawkes Bay, New Zealand.

*Pollination requirement.*—No special pollination requirements known.

Leaf:

*Size.*—Length 3.7 cm; width 2.5 cm.

*Margin.*—Serrate.

*Surface texture.*—Upper surface medium glossy; Lower surface weakly pubescent.

*Color.*—Upper surface green 137A; lower surface yellow-green 146C.

*Petiole.*—Length 1.5 cm; width 0.3 cm; color green-white 157A.

Fruit:

*Size.*—Diameter 8.0 cm; height 7.8 cm.

*Fruit shape.*—Globose conical.

*Position of maximum diameter.*—Just above equator.

*Ribbing.*—Absent.

*Crowning at calyx end.*—Absent.

*Aperture of eye.*—Closed.

*Depth of eye basin.*—1.0 cm.

*Width of eye basin.*—2.3 cm.

*Lenticels.*—Medium, diameter 1 mm; Density 5.5 per $cm^2$.

*Locule.*—Aperture of locule in transverse section closed; Average size of locule is 9.3 mm by 3.7 mm.

*Stalk.*—Diameter 0.3 cm; length 2.5 cm.

*Depth of stalk cavity.*—1.9 cm.

*Width of stalk cavity.*—3.2 cm.

*Bloom of skin.*—Absent.

*Greasiness of skin.*—Absent.

*Ground color of skin.*—Yellow 14C.

*Over color of skin.*—Red 46D stripe with red 46B blush over approximately 95% of surface.

*Flesh.*—Texture crisp, medium juiciness; color yellow 4D.

*Seeds.*—Quantity per fruit 5; teardrop shape; length 1.0 cm, width 0.5 cm; color greyed-orange 166A.

*Aroma.*—Weak.

*Harvest date.*—Last week of March in Hawkes Bay, New Zealand.

*Storage.*—Fruit remains in good condition after 84 days in storage at ±0.5° C.

*Disease/pest resistance.*—None observed.

*Market use.*—Dessert.

We claim:

1. A new and distinct variety of apple plant substantially as shown and described herein.

* * * * *